United States Patent [19]
Christensen et al.

[11] Patent Number: 5,871,751
[45] Date of Patent: Feb. 16, 1999

[54] RENIBACTERIUM SALMONINARUM VACCINE AND METHOD FOR ITS PREPARATION

[75] Inventors: John Mark Christensen, Corvallis, Oreg.; Steve Kaattari, Yorktown, Va.; Jon D. Piganelli, Denver, Colo.; Gregory Wiens, Portland; Jia Ai Zhang, Corvallis, both of Oreg.

[73] Assignee: The State of Oregon Acting By and Through the State Board of Higher Education on Behalf of Oregon State University, Corvallis, Oreg.

[21] Appl. No.: 322,866

[22] Filed: Oct. 12, 1994

[51] Int. Cl.$^6$ .................................................. A61K 39/02
[52] U.S. Cl. ..................... 424/234.1; 424/434; 424/435; 424/442; 424/458; 424/490; 424/827
[58] Field of Search .................... 424/234.1, 827, 424/93.2, 434, 435, 439, 442, 458, 489–502

[56] References Cited

U.S. PATENT DOCUMENTS

| | | |
|---|---|---|
| 4,632,830 | 12/1986 | Formal et al. |
| 5,160,742 | 11/1992 | Mazer et al. ........................... 424/469 |
| 5,399,580 | 3/1995 | Daluge ................................... 514/394 |
| 5,401,727 | 3/1995 | Rorstad et al. ......................... 514/54 |

OTHER PUBLICATIONS

Bacterial Kidney Disease of Salmonid Fish, *Annu. Rev. Microbiol.*, 35:273–298, (1981).

Immunization of Rainbow Trout, *Salmo gairdneri* Richardson, Against Bacterial Kidney Disease: Preliminary Efficacy Evaluation, McCarthy, et al., *J. of Fish Dis.*, 7:65–71 (1984).

Vaccination Against Bacterial Kidney Disease, Munro, et al., *Fish Vaccination*, pp. 124–134, (1988).

Monoclonal Antibody Characterization of a Leukoagglutinin Produced by *Renibacterium Salmoninarum*, Wiens, et al., *Infect. and Immun.*, 59:631–637, (1991).

Bacterial Kidney Disease: The Potential Role of Soluble Protein Antigen(s), Turaga, et al., *J. Fish. Biol.*, 31:191–194 (1987).

Serine Proteinase of *Renibacterium Salmoninarum* Digests a Major Autologous Extracellular and Cell–Surface Protein, Rockey, et al., *Can. J. Micro.*, 37:758–763 (1991).

Variables That Influence Coat Integrity in a Laboratory Spray Coater, Hossain, et al. *Pharmaceutical Technology*, pp. 72–82, (1990).

A Review of Aqueous Coating Techniques and Preliminary Data on Release from a Theophylline Product, Chang, et al., *Pharmaceutical Technology*, pp. 56–68, (1987).

(List continued on next page.)

*Primary Examiner*—Paula K. Hutzell
*Assistant Examiner*—Rachel Heather Freed
*Attorney, Agent, or Firm*—Klarquist Sparkman Campbell Leigh & Whinston, LLP

[57] ABSTRACT

A vaccine and method for treating fish susceptible to infection by *Renibacterium salmoninarum* is described. The vaccine comprises killed microorganisms that lack intact cell-surface-associated protein p57. The vaccine can be used in combination with additional materials, such as, without limitation, adjuvants, plasticizers, pharmaceutical excipients, antigens other than the cells lacking intact cell-surface-associated protein p57, diluents, carriers, binders, lubricants, glidants, aesthetic compounds, such as flavoring and coloring agents, and combinations thereof. The vaccine may be enteric-coated for oral delivery. The enteric coating generally comprises a polymer coating that is impervious to dissolution and/or degradation in the stomach, but is dissolved upon passing to the higher pH environments of the intestine. A preferred embodiment of the vaccine is made using spherical sugar microspheres. The microsphere is coated with a first layer comprising the killed *Renibacterium salmoninarum* microorganisms lacking intact cell-surface-associated protein p57. The sugar microsphere is then coated with a second enteric-coating layer comprising a material that is impervious to dissolution and/or degradation in the stomach of the fish.

22 Claims, 5 Drawing Sheets

OTHER PUBLICATIONS

Evaluation of Fluid–Bed Processes for Enteric Coating System, Mehta, et al., *Pharmaceutical Technology,* 10 pp., (1986).

A Comparison of Rheological and Enteric Properties Among Organic Solutions, Ammonium Salt Aqueous Solutions, and Latex Systems of Some Enteric Polymers, Rong–Kun Chang, *Pharmaceutical Technology,* pp. 62–70, (1990).

Properties of Film–Formers and Their Use in Aqueous Systems, Hermann P. Osterwald, *Pharmaceutical Research,* pp. 14–18, (1985).

The Effect of Plasticizers on Compatibility, Mechanical Properties, and Adhesion Strength of Drug–Free Eudragit E Films, Lin, et al., *Pharmaceutical Research,* vol. 8, No. 9, pp. 1137–1143, (1991).

Simple Rapid Method for the Preparation of Enteric–Coated Microspheres, Maharaj, et al., *Journal of Pharmaceutical Sciences,* vol. 73, No. 1, pp. 39–42, (1984).

Biodegradable Microspheres as a Vaccine Delivery System, Eldridge, et al., *Molecular Immunology,* vol. 28, No. 3, pp. 287–294, (1991).

Large–Scale Field Trial of TY21A Live Oral Typhoid Vaccine in Enteric–Coated Capsule Formulation, Levine, et al., *The Lancet Ltd.,* pp. 1049–1052, (1987).

Efficacy of One or Two Doses of TY21A *Salmonella Typhi* Vaccine in Enteric–Coated Capsules in a Controlled Field Trial, Black, et al., *Vaccine,* vol. 8, pp. 81–84, (1990).

Oral Immunization of Rainbow Trout, *Salmo gairdneri* Richardson, Against Vibriosis with Vaccines Protected Against Digestive Degradation, A. Lillehaug, *Journal of Fish Diseases,* pp. 579–584 (1989).

"The Immune Response of Atlantic Salmon, *Salmo Salar L.,* to the Causative Agent of Bacterial Kidney Disease," *Rebibacterium Salmoninarum,* W.D. Paterson, et al., *Journal of Fish Diseases,* vol. 4, No. 2, Mar. 1981, pp. cover; 99–111.

"Effectiveness of an Oral Enteric Coated Vibrio Vaccine for use in Salmonid Fish," G. Wong, et al., *Immunological Investigations,* vol. 21, No. 4, 1992, pp. cover; 353–364.

"Oral Immunication of Rainbow Trout (*Salmo Gairdneri*) Against an Etiologic Agent of Redmouth Disease", A.J. Ross, et al., *Journal Fisheries Research Board of Canada,* vol. 22, No. 3, 1965, pp. 713–719.

"The Mucosal Immune System: From Fundamental Concepts to Vaccine Development," J.R. McGhee, et al., *Vaccine,* vol. 10, Issue 2, 1992, pp. 75–88.

"Enteric Coated Microspheres as an Oral Method for Antigen Delivery to Salmonids," J.D. Piganelli, et al., *Fish & Shellfish Immunology,* vol. 4, No. 3, May 1994, pp. cover; 179–188.

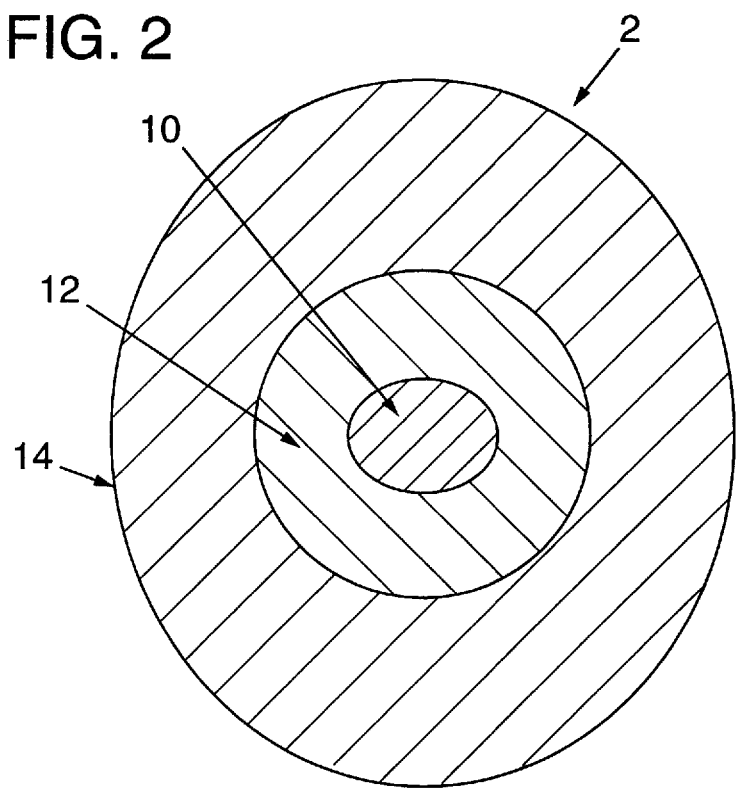

RENIBACTERIUM SALMONINARUM VACCINE AND METHOD FOR ITS PREPARATION

ACKNOWLEDGEMENT OF GOVERNMENT SUPPORT

This invention was made with Government support under USCS-CSRS #92-34123-7665 and USDA (WRAC) #91-38500-6078. The Government may have certain rights in the invention.

FIELD OF THE INVENTION

This invention concerns a vaccine and method for treating fish susceptible to infection by *Renibacterium salmoninarum*.

BACKGROUND OF THE INVENTION

Bacterial kidney disease (BKD) results from infection by *Renibacterium salmoninarum*. BKD is a chronic and systemic disease that generally leads to mortality in juvenile and adult salmonids, both in fresh water and marine environments. Bacterial Kidney Disease of Salmonid Fish, *Annu. Rev. Microbiol.,* 35:273–298. Salmonids are fish of the family Salmonidae, which are soft-finned fishes such as salmon, trout, chars and whitefishes.

*Renibacterium salmoninarum* is a slow-growing gram-positive bacterium. The bacterium is endemic in wild anadromous (migrating up rivers from the sea to breed in fresh water) salmonid populations on both coasts of North America, and has been found in wild Atlantic salmon and sea trout. After infection, *Renibacterium salmoninarum* localizes in the kidney from which infection rapidly becomes systemic.

Farming of marine species is an ancient practice, and aqua culturing of fish has increased significantly over the last twenty years. Commercial aqua culturing requires maintaining high densities of cultured fish. This increases the likelihood of economic loss from diseases such as BKD relative to less-dense fish populations. Although the actual losses attributed to BKD have not yet been calculated, the disease is known to be one of the most important bacterial diseases affecting resident anadromous salmonid stocks in the Pacific Northwest. Because BKD is one of the most prevalent diseases of cultured salmonids, it has had a significant economic impact on the fishing and aqua culture industries.

There still are limited effective methods for controlling BKD despite its economic impact. One reason for this is that the bacteria is capable of adjusting to different conditions as an intracellular parasite, and has the ability to survive and multiply in phagocytic cells (cells that engulf and digest foreign bodies). Current approaches to managing BKD outbreaks include stress reduction, quarantine, chemotherapy (antibiotic treatment), total destruction of the infected population and complete sterilization of the facilities. These approaches to BKD infection are not commercially appealing, and are difficult to administer to large fish populations.

There are no known vaccines effective for treating fish susceptible to infection by BKD, despite the continuous efforts by those skilled in the art. For instance, McCarthy reported an attempt to vaccinate fish susceptible to BKD using two preparations of formalin-inactivated cells of *Renibacterium salmoninarum*. McCarthy et al., *Immunization of Rainbow Trout, Salmo gairdneri, Against Bacterial Kidney Disease: Preliminary Efficacy Evaluation, J. of Fish Dis.,* 7:65–71 (1984). The bacterins were administered without adjuvant by IP-injection, immersion, or two-step hyperosmotic infiltration. No significant protection was afforded by these methods.

Furthermore, Kaattari et al. have treated salmonids with a number of potential immunogens in an attempt to confer immunity to fish susceptible to BKD infection. These immunogens included cell-wall fractions, fractured cells and extracellular products. Kaattari et al., *Development of a Vaccine for Bacterial Kidney Disease, Bonneville Power Administration Final Report,* (1990). These immunogens were administered by intraperitoneal injection, orally, and by immersion with and without adjuvant. None of these early preparations protected fish. In fact, some of these preparations exacerbated the disease.

The route of delivering vaccines often is an important factor for the successful vaccination of fish. Intraperitoneal vaccination is generally the most effective method for vaccinating any species, even though IP vaccination is labor intensive. Immersion is another vaccination method, which is widely used on smaller fish (fish that weigh less than about 10 to 15 grams). The standard immersion method involves exposing fish to the vaccine in aerated standing water for a minimum of 20 seconds. The disadvantage of immersion vaccination is that it is limited by the weight of fish that can be immunized per unit volume of vaccine. And, immersion vaccination usually provides lower levels of immunity than other techniques, due to the stress it causes fish.

SUMMARY OF THE INVENTION

Based on the discussion provided above, it is apparent that a vaccine is needed for protecting salmonids against infection by *Renibacterium salmoninarum*. The present invention provides such a vaccine, as well as a method for treating fish using the vaccine. The vaccine comprises killed *Renibacterium salmoninarum* microorganisms that are devoid of intact cell-surface-associated protein p57. Although vaccines can be made using virtually any strain of *Renibacterium salmoninarum*, operative vaccines have been made using *Renibacterium salmoninarum* microorganisms having the identifying characteristics of a microorganism selected from the group consisting of *Renibacterium salmoninarum* ATCC strain 33209 and *Renibacterium salmoninarum* D6 isolate. The vaccine can be used in combination with additional materials, such as, without limitation, materials selected from the group consisting of adjuvants, plasticizers, pharmaceutical excipients, antigens other than cells lacking intact cell-surface-associated protein p57, diluents, carriers, binders, lubricants, glidants, aesthetic compounds, such as flavoring and coloring agents, and combinations thereof.

The vaccine also may be enteric-coated for oral delivery. The enteric coating protects the vaccine from proteases and from the relatively low pH levels of the stomach. This allows the vaccine to reach the hindgut associated with lymphoid tissue, which maximizes the effectiveness of the vaccine for protecting fish. The enteric coating typically comprises a polymer coating that is unaffected by acidic pH, but which is dissolved upon passing to the higher pH environments of the pyloric caecum and intestine. The pH of salmonid stomachs varies from about 1.5 to about 4.8. The physiologic pH rapidly increases in the intestine of the fish to pH values of greater than about 5, and continues to increase to a pH of about 8 in the anus region of the fish. As a result, the polymer coating should not dissolve until in an environment where the pH is greater than about 5.0 and less than about 8. As a result, enteric-coating materials useful for the invention may be selected from the group consisting of enteric-coating materials, particularly polymeric materials, that dissolve in a liquid having a pH of from about 5 to about 8.

Oral administration is a generally preferred method of vaccinating fish against BKD using vaccines of the present invention. Oral vaccinations provide an ideal method for the mass administration of the vaccine to fish. Oral vaccination also is not limited by the size of the fish that can be handled, and it reduces the stress on the fish associated with immersion and IP vaccination. Furthermore, oral vaccines offer the additional advantage of stimulating mucosal immunity.

A preferred embodiment of the vaccine is made by coating spherical sugar microspheres (beads) with vaccine formulations. The beads can be virtually any material, now known or hereinafter developed, that is useful for delivering pharmacological materials. By way of example and without limitation, dextrose beads have been shown to be useful for forming such beads. The beads generally have a mesh size of from about 10 to about 60 mesh, preferably from about 20 to about 35 mesh, and even more preferably from about 25 to about 30 mesh.

The beads generally are coated with a first layer comprising the killed *Renibacterium salmoninarum* microorganisms lacking intact cell-surface-associated protein p57. This coating also may comprise additional materials, such as materials selected from the group consisting of adjuvants, plasticizers, pharmaceutical excipients, antigens other than cells lacking intact cell-surface-associated protein p57, diluents, carriers, binders, lubricants, glidants, aesthetic compounds, such as flavoring and coloring agents, and combinations thereof. For instance, a disintegrant or a super disintegrant often is used to help disperse the material once it is ingested. One example of a super disintegrant is sodium starch glycolate.

The bead is then coated with a second coating layer comprising an enteric-coating layer. This layer generally is a polymeric layer wherein the polymer is impervious to dissolution and/or degradation in the stomach of the fish, but does dissolve upon passing out of the stomach. That is, the polymer generally is impervious to dissolution in an aqueous media having a low pH, such as a pH of less than about 5, but is dissolved by an aqueous media having a pH value of from about 5 to about 8. There are numerous materials that are potentially useful for coating the beads as discussed in detail below. Solely by way of example, a polymeric material currently known to be suitable for coating the beads is poly(methylacrylic acid-ethyl acrylate).

A preferred embodiment of the second bead coating comprises a mixture that includes about 2 weight percent to about 50 weight percent poly(methylacrylic acid-ethyl acrylate), less than about 50 weight percent of a plasticizer, such as less than about 10 weight percent dibutyl sebacate and less than about 10 weight percent triethyl citrate, and a material that reduces particle agglomeration during the coating process, such as talc. Unless noted otherwise, the weight percents stated in this application are based on the final dry weight of the coated beads.

One skilled in the art also will realize that the BKD vaccine of the present invention can be used in combination with immunostimulants, such as β-glucans. The immunostimulant may be incorporated into the formulations coated onto the microspheres so that the immunostimulant is released by the beads following the administration thereof to fish susceptible to infection by *Renibacterium salmoninarum*. The beads can be coated so that the immunostimulant is released prior to the release of the BKD vaccine. This is believed to prime the immune system. Alternatively, the BKD vaccine of the present application may be released prior to the immunostimulant. As still another possibility, immunostimulants may be administered by a method other than that chosen for the delivery of the BKD vaccine. For instance, the BKD vaccine might be orally administered and the immunostimulant administered by IP injection or by immersion, either prior to, simultaneously with, or after the administration of the BKD vaccine.

The present invention also provides a method for reducing the infection of fish susceptible to infection by virulent strains of *Renibacterium salmoninarum*. A preferred embodiment of the method comprises first heating *Renibacterium salmoninarum* microorganisms to a temperature of at least about 37° C. to produce *Renibacterium salmoninarum* microorganisms lacking intact cell-surface-associated protein p57. Nonpareil sugar beads, having a preferred mesh size of from about 25 to about 30, then are coated with a first layer comprising a mixture of a super disintegrant and *Renibacterium salmoninarum* microorganisms lacking intact cell-surface-associated protein p57. The beads are then coated with a second layer comprising a pH-sensitive polymeric material that is dissolved by an aqueous media having a pH of about 5.0 or greater, thereby producing an enteric-coated vaccine. The coated beads are orally administered to fish in an amount sufficient to reduce the infection by fish susceptible to infection by *Renibacterium salmoninarum*. The method may also comprise the step of treating fish susceptible to infection by *Renibacterium salmoninarum* with an immunostimulant either before, simultaneously with, or after the step of administering the vaccine to fish.

BRIEF DESCRIPTION OF THE DRAWINGS

FIG. 2 is a schematic representation of an oral enteric-coated vaccine according to the present invention.

DETAILED DESCRIPTION OF THE PREFERRED EMBODIMENTS

Figure 1A:
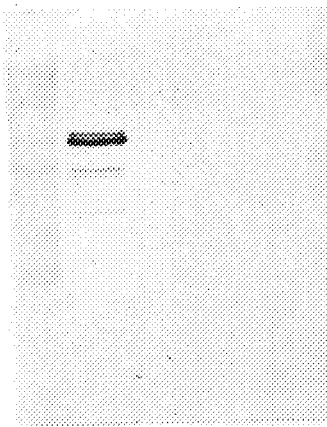
FIGS. 1A–1B is a Western blot (A) and total protein stain (B) of *Renibacterium salmoninarum* cells after treatment at 37° C. followed by formalin incubation at 17° C.
Figure 1B:
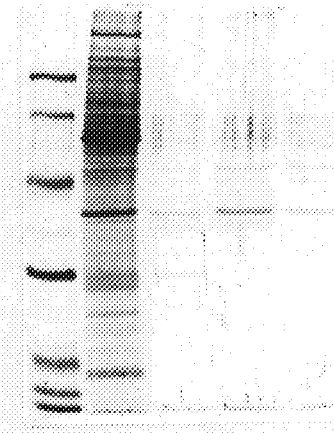

The present invention provides the first known vaccine and method for effectively protecting fish susceptible to infection by *Renibacterium salmoninarum* microorganisms. A detailed discussion follows concerning how to make the claimed vaccine, as well as how to administer the vaccine to fish. Experimental data also is presented which demonstrates that the vaccine is effective for protecting fish from infection by *Renibacterium salmoninarum*.

I. DEFINITIONS

A number of definitions are provided below. These definitions are provided solely for the convenience of persons reading this disclosure. These definitions are not intended to narrow the scope of such terms to definitions less encompassing than that understood by persons skilled in the art.

1. "Killed vaccines" generally refer to microorganisms which have been heat-treated and thereafter treated with some chemical agent, such as formalin. *Renibacterium salmoninarum* is heat sensitive. It currently is believed that heat treatment alone, such as heating to temperatures greater than about 35° C., is sufficient to kill the bacterium. However, solely for the purpose of caution, the heat-treated bacterium also usually are treated with a chemical agent to produce the killed vaccine.

2. "Protective immunity" is the condition induced by the administration of a vaccine to a fish wherein the susceptibility of the fish to infection by a particular pathogen is reduced.

3. "Susceptible fish" are those species of fish of which *Renibacterium salmoninarum* is a pathogen and in which the vaccines of the present invention are capable of inducing protective immunity. That is, the microorganism is capable of causing Bacterial Kidney Disease (BKD) in such a fish and the fish is capable of being protected from such disease by vaccination with the vaccines of the present invention. For the purposes of the present invention, "susceptible fish" includes all salmonid fish. Salmonid fish include, but are not limited to, pacific salmon in general (Oncorhynchus sp.), such as rainbow trout (*Oncorhynchus mykiss*), chinook salmon (*Oncorhynchus tshawytscha*), coho salmon (*Oncorhynchus kisutch*) sockeye salmon (*Oncorhynchus nerca*) and atlantic salmon (*Salmo salar*). Both the chinook and coho salmon appear to be particularly susceptible to infection.

4. "Susceptibility to infection" describes the condition of being a host for a particular pathogen and of suffering injury from the disease caused by that pathogen. The condition of "susceptibility to infection" encompasses a range of susceptibilities. The degree of susceptibility of a particular fish to infection by a particular pathogen may be determined by calculating the $LD_{50}$ value for this pathogen. Fish species less susceptible to infection by a particular pathogen will have a higher $LD_{50}$ for that pathogen than a more susceptible fish species.

5. "p57$^-$" is a short-hand notation which refers to cells of *Renibacterium salmoninarum* which lack intact cell-surface-associated protein p57.

6. "p57$^+$" is a short-hand notation which refers to cells of *Renibacterium salmoninarum* which include cell-surface protein p57.

7. "Adjuvant" as used herein refers to any material that enhances the action of a drug or antigen.

8. "Pharmaceutical Excipient" refers to any inert substance that is combined with an active drug or antigen for preparing an agreeable or convenient dosage form.

II. MATERIALS AND METHODS

A. Bacterial Strains

Bacterial Kidney Disease (BKD) is caused by a fastidious, slow growing bacterium, *Renibacterium salmoninarum*. The bacteria presents itself as a facultative (i.e., the bacteria is capable of an adaptive response to various environments) intracellular parasite, which also has the ability to survive and multiply within the phagocytic cell. *Renibacterium salmoninarum* is a gram-positive, short rod (0.08–1.0×0.3–0.5 µm) bacterium. The bacterium is nonmotile, asporogenous, non-acid fast and encapsulated. The guanine-plus-cytosine (G+C) content of the bacteria averages about 53-mole percent.

It is likely that all isolates of *Renibacterium salmoninarum* can be used to make vaccines according to the present invention. All strains of *Renibacterium salmoninarum* produce cell-surface protein p57. And, all strains of *Renibacterium salmoninarum* are significantly genetically homogenous, more so than other bacterium, regardless of where the bacteria are isolated. The genetic homogeneity of the *Renibacterium salmoninarum* is a trait fairly unique to the organism. Persons skilled in the art have tried to develop antibodies useful for distinguishing between strains of the bacterium. So far, these efforts have proved fruitless. Thus, "strains" when used in connection with *Renibacterium salmoninarum* simply refers to the location where the bacterium were isolated, and not to some inherent physiological difference between the isolated microorganisms.

Solely to provide specific guidance as to *Renibacterium salmoninarum* isolates that have been used to develop vaccines, a first such isolate was cultured from chinook salmon (*Oncorhynchus tsawytscha*, Oregon) and has ATCC strain number 33209. A second isolate, isolate D6, was isolated from coho salmon (*Oncorhynchus kisutch*, held in salt water in Oregon). The D6 isolate was obtained from C. Banner of Oregon State University. The D6 isolate also is discussed in Wiens et al.'s *Monoclonal Antibody Analysis of Common Surface Protein(s) of Renibacterium salmoninarum*, Fish Pathology, 24:1–7 (1989), which is incorporated herein by reference. All strains used to produce vaccines were stored at −70° C. prior to culture.

The following Example 1 describes a method for culturing *Renibacterium salmoninarum*. This and all subsequent examples should, in no way, be construed to limit the scope of the present invention to the particular embodiments described.

EXAMPLE 1

*Renibacterium salmoninarum* ATCC 33209, or Isolate D6, was grown in one-liter volume portions using a 2.5 liter low form, VWR culture flask. The *Renibacterium salmoninarum* cultures were grown with intermittent shaking at 17° C. using a KDM-II growth medium prepared according to the method of Evelyn, except without serum supplementation. This medium is discussed in Evelyn et al.'s *An Improved Growth Medium for the Kidney Disease Bacterium and Some Notes on Using the Medium*, Bull. Int. Epiz. 78:511–513 (1977), which is incorporated herein by reference. The bacteria were grown until an optical density of from about 0.4 to about 0.8 was generated at about 525 nm. This required approximately 7 to 8 days. Seven one-liter volumes of bacteria from the 2.5-liter low-form VWR culture flasks were combined, and then pelleted by centrifugation at 6,000×g for about 30 minutes. The pelleted cells were then resuspended in 100 ml of cold, phosphate-buffered saline solution (PBS; 0.85% NaCl, 10 mM $NaPO_4$, pH 7.2). The cells were then centrifuged a second time at 6,000×g. Thereafter, the cells were placed in microfuge tubes and frozen at −70° C. for storage.

B. Bacterial Extracellular Preparations as Vaccination Control

The vaccine preparations of the present invention, which are described in detail below, were evaluated relative to a number of control formulations, including extracellular preparations from *Renibacterium salmoninarum*. An extracellular protein (ECP) preparation for use as a control was prepared according to the method of Daly et al.'s *Agglutination of Salmonid Spermatozoa by Renibacterium salmoninarum*, J. Aquatic Animal Health, 1:163–164 (1989), which is incorporated herein by reference. The following Example 2 describes a method for obtaining the ECP.

EXAMPLE 2

2 to 4 grams of wet bacterial cells were washed with 100 ml of sterile phosphate buffer saline and then pelleted by centrifugation at 6,000×g for 30 minutes. The centrifuged cells were then resuspended in 100 ml of distilled and deionized water and placed on ice for about one hour. The cells were then repelleted by centrifugation at 6,000×g. The supernatant was removed and cell-surface proteins were precipitated with the addition of powdered ammonium sulfate. The resulting ECP extract was dialyzed three times against phosphate buffer saline and filter sterilized by passing the extract through a 0.45 μm filter. The protein concentration was then determined by the method of Lowry et al.

C. Preparation of Killed Vaccine Lacking Intact Cell-Surface-Associated Protein P57

A major component of the ECP is a protein having a molecular weight of about 57 kDa. This protein also is known to be a major cell-surface protein. Without limiting the present invention to one theory of operation, it currently is believed that the present vaccine protects fish where previous attempted vaccines and vaccination methods have failed because cell surface protein p57 is removed from the bacterial cells before being administered to fish as a vaccine.

Heat treatment is a currently preferred method for removing the cell-surface protein p57. However, the present invention encompasses any methods now known or hereafter developed for removing p57. Although the temperature used to remove the protein may vary, a temperature of about 37° C. is believed to be the optimal temperature for activating an autologous serine protease, and therefore for cleaving off the cell-surface protein. See Rockey et al., *Characterization of a Renibacterium salmoninarum Serine Protease Which Digests a Major Autologous Extracellular and Cell-Associated Protein, Can. J. Micro.,* 37:758–763 (1991), which is incorporated herein by reference.

The vaccine of the present invention is administered as a killed vaccine. The present invention encompasses any methods now known or hereafter developed for killing *Renibacterium salmoninarum* cells for use as a vaccine. However, it has been determined that heating the cells to a temperature of about 37° C. kills the microorganism. *Renibacterium salmoninarum* is a relatively heat-sensitive organism. In fact, it is likely that temperatures of less than about 37° C. can be used to kill the bacterium. However, as the temperature is lowered, the time required to kill the organisms increases. If heat treatment alone is used to kill the vaccine, then the temperature likely should not be increased to be much above 55° C. Otherwise, the serine protease activity may be hindered. As a result, the removal of the p57 cell-surface-associated protein would be affected.

In order to insure that the bacteria were killed prior to administering the vaccine derived therefrom to fish, the heat-treated cells first also were fixed with formalin. The step of formalin fixing likely is a superfluous step, and it currently is believed that heating the cells is a sufficient method for killing the bacterial cells.

The following Example 3 describes a method for preparing killed $p57^-$ bacterial cells.

EXAMPLE 3

Frozen harvested cells were prepared as described above in Example 1. The frozen cells were thawed from −70° C. and microfuged at 6,000×g. The centrifuged cells were then weighed and resuspended in a sufficient amount of cold, sterile phosphate buffer to obtain a concentration of about 200 mg cells/ml. The cells were then heated to a temperature of about 37° C., and this temperature was maintained for about 48 hours. After the heating step had been completed, the cells were again microfuged at 6,000×g, and then resuspended in a 3% formalin-phosphate buffered saline solution. The formalin-cell mixture was then cooled to a temperature of about 17° C., which was maintained for about 10 hours. The cells then were repeatedly washed with phosphate buffered saline solutions and reweighed.

FIG. 1 shows a Western blot (A) and total protein stain (B) of *Renibacterium salmoninarum* cells following treatment at 37° C. and formalin incubation at 17° C. as described above in Example 3. The Western blot was probed with monoclonal antibody 4D3, which recognizes p57. The lanes represented on the gels are as follows: Molecular weight; Lane 1 shows untreated *Renibacterium salmoninarum* cells; lanes 2–4 illustrate three separate treatments of *Renibacterium salmoninarum*. Lanes 2–4 on both the Western blot and the total protein stain clearly indicate the absence of a band corresponding to p57. This demonstrates that the method described in Example 3 effectively removes p57 to below detectable limits, thereby producing $p57^-$ *Renibacterium salmoninarum* cells.

D. Antigen Preparation for Vaccine Comparisons

In order to determine the effectiveness of the killed *Renibacterium salmoninarum* cells for developing an intraperitoneal vaccine, bacterial antigens were emulsified in Freund's incomplete adjuvant (FIA) using a Virtis 23 mixer set at 100 units for four minutes. The putative antigens used for the intraperitoneal vaccination consisted of approximately 500 μg of heat-treated *Renibacterium salmoninarum* cells produced as described above in Example 3, 50 μg of cell surface extract obtained as described above in Example 2, and 50 μg from extracellular protein extracted from culture supernatants.

E. IP Vaccination and Challenge

Coho salmon were injected with the putative antigen preparations in a total volume of about 0.1 ml. The fish were injected IP and intramuscularly, with a total of about 0.05 ml at each location, using a 22 gauge needle. Booster injections were then given to the fish 45 days after the primary injection. The booster injection consisted of about one half of the volume of the antigen or control preparations used in the primary injection, although the total volume of material injected was the same in both the primary and booster injections. The fish then received a secondary boost 10 days after the first booster shot was administered.

The vaccinated fish were challenged by IP injection. The progress of BKD in fish challenged by natural methods is slow. The onset of the disease may take as long as a year or more, which makes laboratory testing impractical. As a result, the fish were initially challenged by IP injection to accelerate the onset of the disease. The *Renibacterium salmoninarum* used for the challenge were grown for 7 days in KDM-II and thereafter washed with PBS. The cells were then suspended in sterile PBS to obtain a final optical density of about 0.2 at 525 nm. The fish were then IP challenged with a challenge dose of about $4.1 \times 10^6$ cfu/ml. The results of this challenge experiment are summarized in FIG. 3.

FIG. 3 shows the percent survival of coho salmon immunized with various potential immunogenic materials obtained from *Renibacterium salmoninarum*. Three tanks of salmon (40 salmon/tank) were injected with the various materials. The fish were injected with either saline emulsified in Freund's incomplete adjuvant (see graph 3A), extracellular protein in Freund's incomplete adjuvant (see graph 3B), virtually pure p57 obtained from cell wash and emulsified in Freund's incomplete adjuvant (CW, see graph 3C), and p57⁻ *Renibacterium salmoninarum* cells in Freund's incomplete adjuvant. Graphs 3A–3D are illustrated having error bars which represent two standard errors about the mean for the three trials.

Figure 3A:
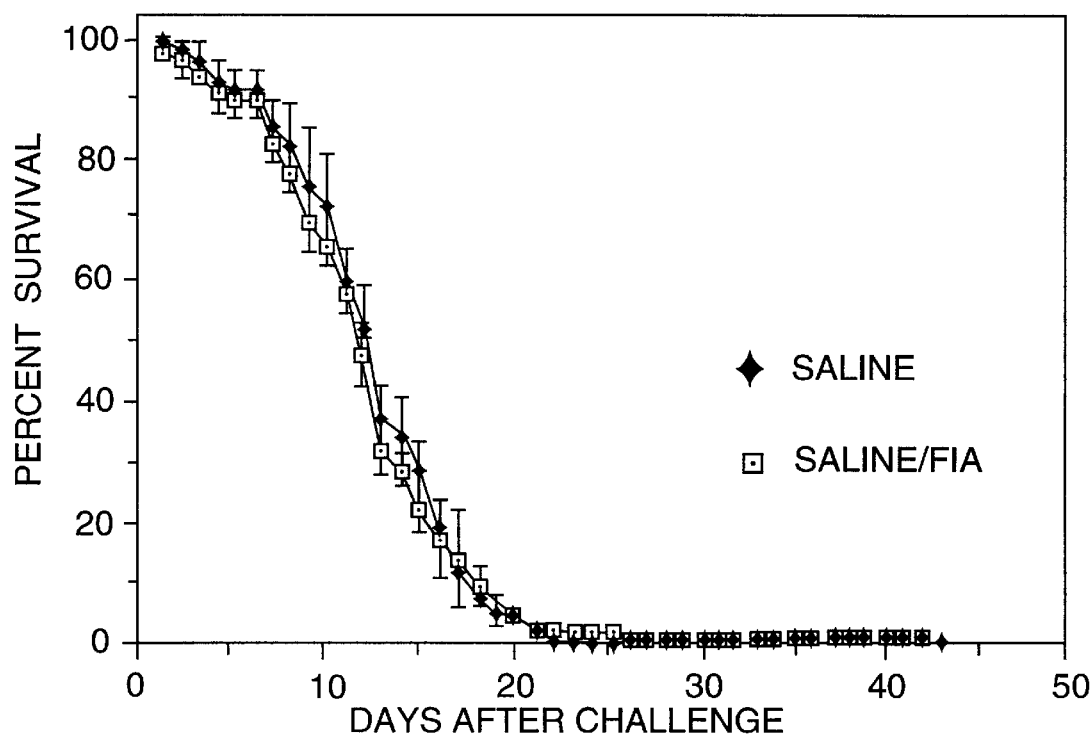
FIGS. 3A–3D are graphs showing the percent survival of fish over time following challenge with *Renibacterium salmoninarum*, wherein the challenged fish had been IP injected with one embodiment of a vaccine according to the present invention.
Figure 3B:
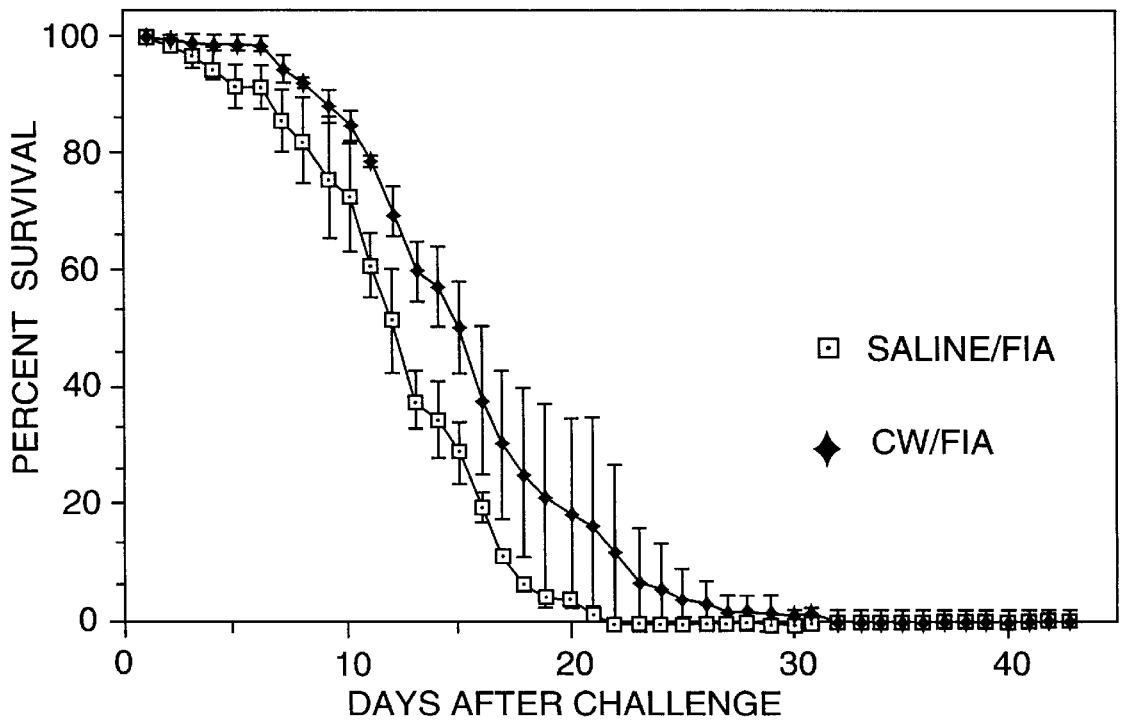
Figure 3C:
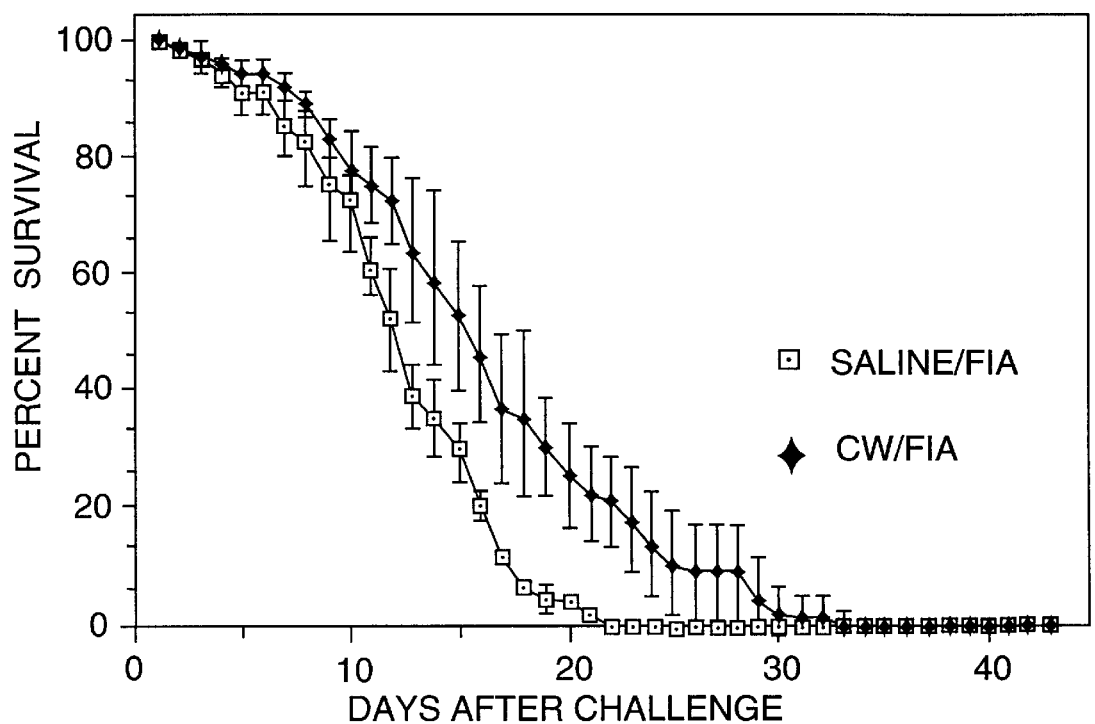
Figure 3D:
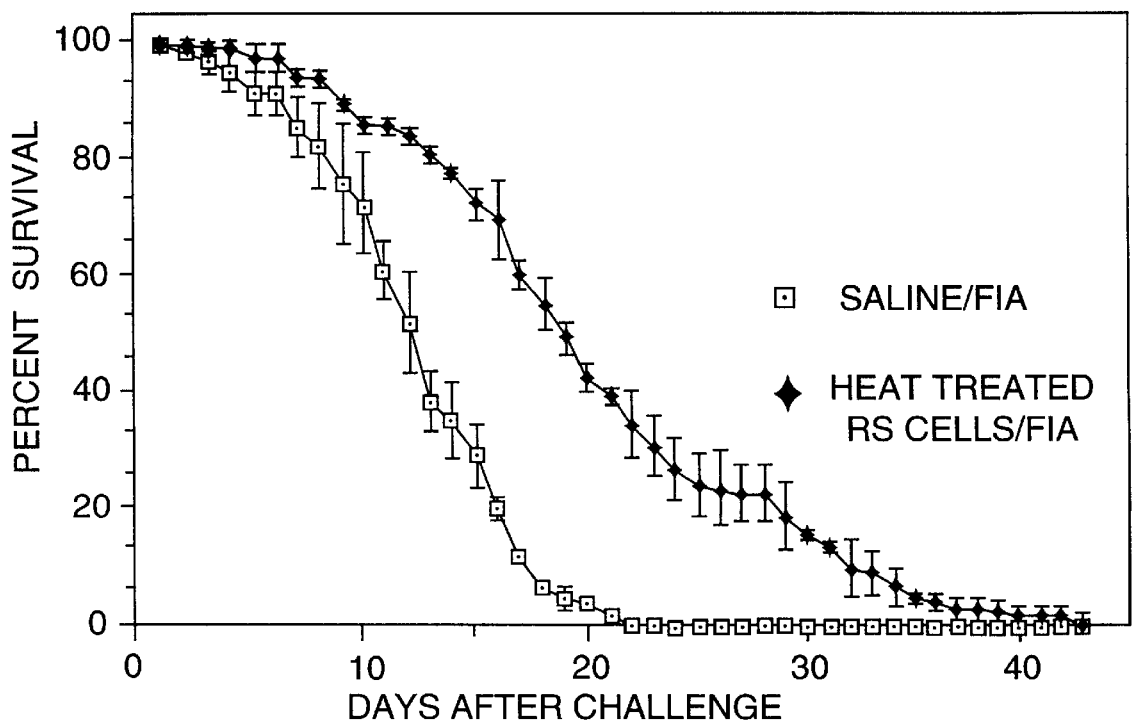
Figure 4:
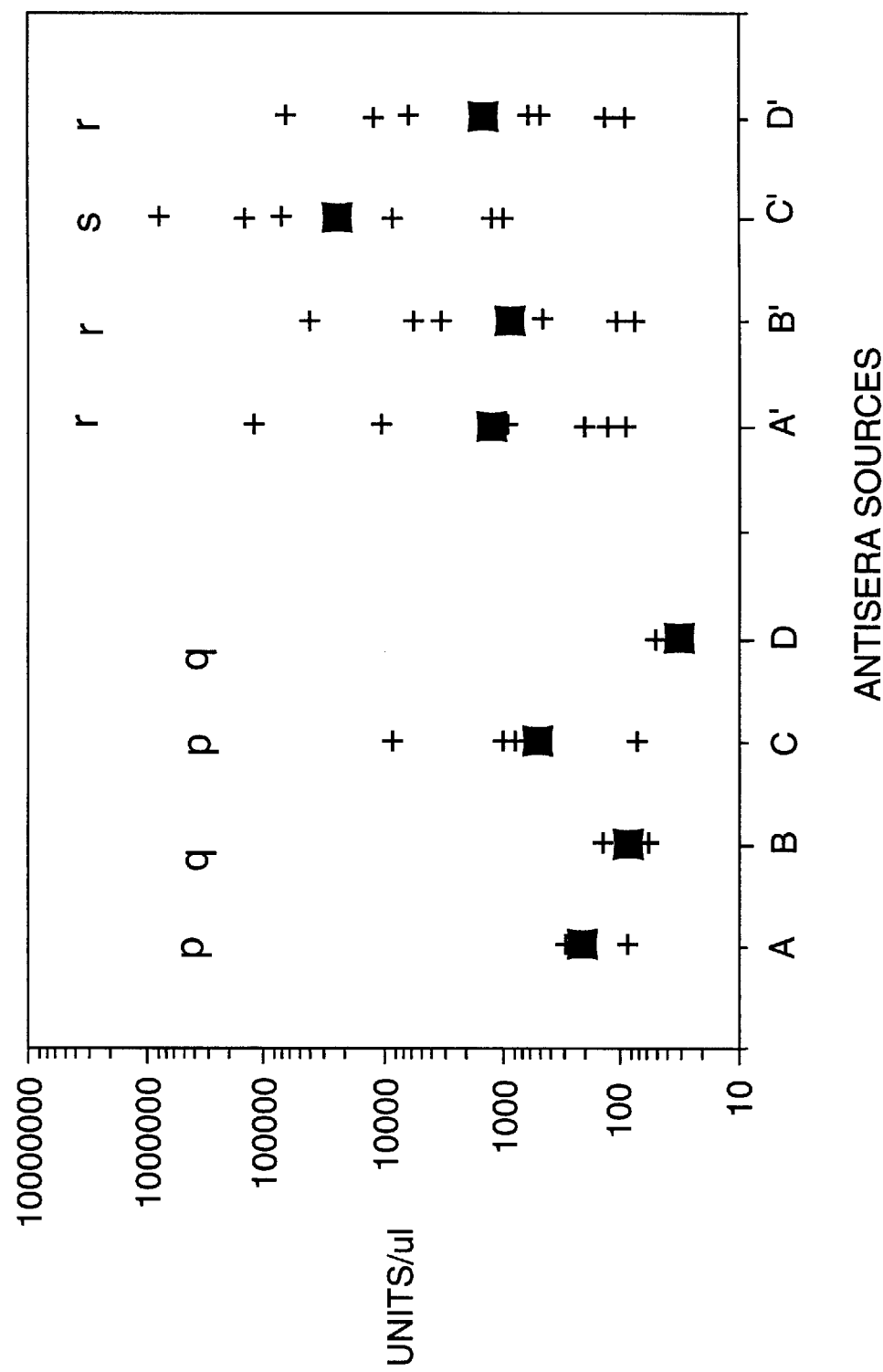
FIG. 4 is a graph of titers of *Renibacterium salmoninarum* antibodies from chinook salmon immunized with p57⁻ or p57⁺ whole *Renibacterium salmoninarum* cells.

The results summarized by FIG. 3 indicate that fish receiving p57⁻ had a significantly increased mean time to death following challenge with live *Renibacterium salmoninarum*. FIG. 3D appears to show that all fish IP treated with p57⁻ cells die; however, one reason for this is because the fish were challenged with a relatively large concentration of pathogen that would be expected to cause death, even if the fish were successfully immunized by the vaccine. In other words, the large pathogen concentration used for the challenge was intended to cause death; otherwise, the time required for the challenged fish to die would be too long for practical laboratory investigation. However, it is clear from FIG. 3D that the fish treated by IP immunization had a significantly enhanced mean time to death following pathogen challenge.

FIG. 4 depicts the units of activity/μl for titers of anti-*Renibacterium salmoninarum* antibodies produced upon immunization of chinook salmon. Two groups of chinook salmon (60 fish per group) were IP immunized using either $p57^+$ or $p57^-$ cells. After 86 days following injection, serum samples were taken and antibody titers were then determined using the procedure of Kaattari et al. The fish then received a booster shot on day 100 post initial inoculation. On day 128, serum samples were again taken and the data is presented in FIG. 4. This data clearly shows that salmon demonstrate a 20-fold higher titer to $p57^-$ cells (C') than do sera taken from fish injected with $p57^+$ cells (A') . More specifically, fish receiving $p57^-$ cells had an average titer of about 25,703 units of anti*Renibacterium salmoninarum* activity/μl. Fish receiving $p57^+$ cells had an average titer following receipt of the booster shot of about 1,276 units of anti-*Renibacterium salmoninarum* activity/μl. Thus, removing p57 cell-surface protein from the bacterial cells used as immunogenic material for treating salmonids significantly increased the immunogenicity of the *Renibacterium salmoninarum*. Moreover, although oral administration of the $p57^-$ bacterial cells is a preferred delivery method, IP injection also effectively elicits an immune response in fish receiving the bacterial cells.

F. Preparation of Oral Vaccine

After the results were obtained for IP vaccination and challenge, a decision was made to try and develop an oral vaccine. Although the present invention is not limited to administering the vaccine orally, oral administration is a currently preferred delivery method. One reason for this is that oral administration apparently stimulates the gut associated lymphoid tissue (GALT) to a greater extent than does IP injection.

Microspheres have been used for the oral delivery of the present vaccine. There are several advantages for using microspheres, including:

(1) The microspheres release the antigen which can then be taken up in the GALT, which is an important part of the secretory immune system.

(2) Entrapped antigens are protected from being degraded by the acidic environment of the stomach.

(3) Plural antigens can be administered at the same time.

(4) Pharmaceutical excipients, such as super disintegrants, can be applied to the microspheres.

(5) Additional materials, such as adjuvants, may be administered along with the specific antigen of interest.

(6) Controlled/sustained-release formulations are possible.

The present invention provides a BKD vaccine that can be administered orally after the antigenic material is applied to microspheres and subsequently enteric-coated such that the antigenic materially is encapsulated thereby to produce an enteric-coated antigenic microsphere (ECAM). A schematic diagram of one embodiment of an ECAM is illustrated in FIG. 2 as ECAM 2. The illustrated embodiment of the ECAM 2 comprises a sugar bead 10 of conventional type, at least a first antigen coating 12, and an enteric protective layer 14.

One skilled in the art will realize that a number of sugar beads potentially are useful for forming ECAMs. However, without limitation, a currently suitable sugar bead is an NF sugar sphere which can be obtained commercially from Ingredient Technology Corporation, of Pennsauken, N.J. The illustrated sugar beads 10 of FIG. 2 are dextrose beads.

The size of the bead is an important consideration for selecting an appropriate sugar microsphere. Certain bead sizes have been found to be too big to pass through the pyloric sphincter of the fish, and therefore may not effectively confer immunity to fish treated with such beads and an oral vaccine. Presently, it appears that a microsphere having a mesh size of from about 10 to about 60 mesh, preferably from about 20 to about 35 mesh, and even more preferably from about 25 to about 30 mesh, will perform satisfactorily for forming ECAMs of the present invention.

Sugar beads 10 are coated with a first antigen coating 12. As will be apparent from the preceding discussion, the antigens of choice for the present invention are $p57^-$ killed bacterial cells. Sugar spheres have been coated with this, and other potential immunogenic materials, using a fluidized bed spray coater. The actual coater used for coating such microspheres was obtained from Labline/PRL, of Melrose Park, Ill. The antigens were applied to the sugar spheres typically as a gelatinized solution, such as about a 4% weight/volume solution.

After the antigen coating 12 has been applied to the sugar bead 10, an enteric-protective layer 14 is then be applied to the sugar bead. As with the selection of the sugar bead, one skilled in the art will realize that a number of enteric-coating agents may be used. The present invention is directed to any vaccine comprising $p57^-$, including any such material that has been enteric-coated with any coating material now known or hereafter developed.

However, solely by way of example, currently suitable enteric-coating materials are non-toxic polymeric materials which resist dissolution at the pH of the stomach, but which are dissolved once the material passes from the stomach to the pyloric caecum and intestines. Preferably, the polymeric material is dispersible in an aqueous system without the use of organic solvents. The Environmental Protection Agency does not recommend using organic solvents for use in spray-coating procedures. Organic solvents also add to the expense of producing the vaccine.

Table 1 below provides a non-exhaustive list of enteric-protecting polymeric materials currently believed to be useful for forming the vaccines of the present invention.

TABLE 1

ENTERIC COATING POLYMERIC MATERIALS (1) Cellulose Acetate phthalate (CAP)

(2) Hydroxypropylmethyl Cellulose Phthalate (HPMCP)

(3) Carboxymethylethyl Cellulose (CMEC)
(4) Hydroxypropylmethyl Cellulose Acetate Succinate (HPMC-AS)
(5) Cellulose Acetate Trimellitate (CAT)
(6) Polyvinyl Acetate Phthalate (PAP)

EUDAGRIT BRAND POLYMERS (7) EUDAGRIT L-30-D and l 100-55
  Poly(ethylacrylate, methacrylic acid),
  [copolymer having a 1:1 ratio of monomers; dissolves at pH=5.5]
(8) EUDAGRIT L 12.5 and L 100
  Poly(methacrylic acid,
  methylmethacrylate) tend to dissolve at pH of from about 5.8–6.0.
(9) EUDRAGIT E, RL, RS and NE.

Additional information concerning materials useful for forming coatings for the present invention can be obtained by consulting (1) Osterwald's *Properties of Film-Formers and Their Use In Aqueous Systems, Pharmaceutical Research*, 2:14–18 (1985), and (2)*Aqueous Polymeric Coatings for Pharmaceutical Dosage Forms*, edited by J. W. McGinity, Marcel Publishing (1989). Each of these references is incorporated herein by reference.

A polymeric material that has been used to form vaccines for the present invention is poly(methacrylic acid-ethylacrylate). This material is commercially available from Röhm Pharma of Weiterstadt, Germany, as EUDRAGIT™ L-30D. The polymeric material was applied in the same manner as the antigen to form enteric-protected sugar spheres.

Persons skilled in the art also will realize that additional materials can be used in combination with the enteric-coating materials to form the enteric-coated antigen microspheres. For instance, plasticizers often are used to form pharmaceutical preparations. Pages 17 and 68 of *Aqueous Polymeric Coatings for Pharmaceutical Dosage Forms*, supra, provide a list of plasticizers commonly used for pharmaceutical preparations. The following Table 2 also provides a non-exhaustive list of useful plasticizers.

TABLE 2

PLASTICIZERS (1) Polyethylene glycol 200 (PEG 200; 200 refers to the average molecular weight)
(2) Polyethylene glycol 400 (PEG 400)
(3) Polyethylene glycol 1000 (PEG 1000)
(4) Polyethylene glycol 4000 (PEG 4000)
(5) Polyethylene glycol 6000 (PEG 6000)
(6) Propylene glycol
(7) PVPK-90
(8) Glycerin or Glycerol
(9) Diethyl Phthalate
(10) Oleic acid
(11) Isopropyl myristate
(12) Liquid paraffin or mineral oil
(13) Triacetin
(14) Glycerol monostearate
(15) Dibutyl Sebacate
(16) Triethyl citrate
(17) Tributyl Citrate
(18) Acetylated monoglyceride
(19) Dibutyl phthalate
(20) Acetyl tributyl citrate
(21) Castor oil
(22) Glycerol tributyrate Disintegrants, including materials generally considered by those skilled in the art to be super disintegrants, also often are used in combination with the enteric-coating material to facilitate the disintegration of the microsphere and release of the vaccine. Any disintegrant now known or hereafter developed likely will work for forming the vaccines of the present invention. Solely by way of example, sodium starch glycolate (SSG, Explotab®, Edward Mendell) is a super disintegrant currently known to be useful for practicing the present invention.

Vaccines produced using spray-coating devices tend to agglomerate while air-entrained. To alleviate the agglomeration, a "free-flowing" material may be added to the coating mixture. A number of "free-flowing" materials potentially are useful for practicing the invention, and the invention should be interpreted as being broad enough to cover any such additives now known or hereafter developed. Solely by way of example, useful materials for preventing the agglomeration of the vaccines during the spray coating operation may be selected from the group consisting of talc, magnesium stearate, silicone, silicon oxide, and combinations thereof. For the present invention, it has been found that talc efficiently alleviates agglomeration during the coating process, is readily available, and hence is a currently preferred material for alleviating agglomeration.

Example 4 below describes a method for producing an ECAM according to the present invention. EXAMPLE 4

100 grams of 25–30 or 30–35 mesh size NU-PARELL® PG, NF Sugar Spheres were obtained from Ingredient Technology Corporation of Pennsauken, N.J. These sugar spheres were loaded into a Lab-line/PRL fluid-bed bottom spray coater preheated to a temperature of about 60° C. (microspheres also have been coated at temperatures of from about 37° C. to about 70° C.). The temperature of the sugar spheres was allowed to equilibrate with that of the coating unit. A 22.5 ml aqueous mixture of a vaccine and a suitable binder comprising from about 0.03 weight percent to about 4 weight percent BKD vaccine (p57$^-$ cells, weight percent based on the weight of the sugar beads to be coated in the coating chamber), and gelatin was prepared. A super disintegrant (either 5%, 9% or 12%) sodium starch glycolate (SSG, Explotab®, Edward Mendell, Patterson, N.Y.)) was added to this mixture. The 12% SSG released antigen the fastest, and hence is a preferred amount of SSG disintegrant useful for the present invention. The sugar spheres were then placed into the preheated coating apparatus, which was equipped with an 0.8 mm bottom spray nozzle. The operating nozzle pressure of the apparatus was about 18± psi, and the blower speed was set at 40 to 50% of full capacity. This caused free movement of the beads in the coating machine. The BKD vaccine was constantly delivered to the nozzle by a peristaltic pump (Gilson Medical Electronics, Middleton, Wis.) at rate of about 2 to 3 ml/minute.

Once the sugar-sphere coating process was completed, the pellets were dried in the coating chamber for about 5 minutes using the same temperature and air flow stated above. The antigen-coated beads were removed from the coating chamber and kept overnight in an oven that was heated to a temperature of 37° C. This helped remove residual moisture before the enteric-coating was applied.

An enteric-coating mixture was then formed comprising about 30% (w/v) Eudragit L-30D (PMA-EA, Eudragit™ L-30D, Röhm Pharma, Weiterstadt, Germany), less than about 10 weight percent dibutyl sebacate (DBS, Sigma Chemical Co.), less than about 10 weight percent triethyl citrate (TEC, Aldrich Chemical Company, Inc.) and talc (Matheson Coleman & Bell, East Rutherford, N.J.). This mixture was applied to the antigen-coated sugar bead in the same manner as the antigen was applied, thereby forming an ECAM according to the present invention. About 20% (w/w) Eudragit L-30D was applied to the beads based on the final dry weight of antigen-loaded beads.

The following enteric-coating formulations have been applied to sugar beads to from coated vaccine microspheres.

TABLE 3

ENTERIC-PROTECTED FILM POLYMER FORMULATION FOR 100 G OF 30–35 MESH-SIZE ANTIGEN-COATED VACCINE BEADS

| COMPONENTS | GRAMS | WT. IN DISPERSION |
|---|---|---|
| EUDAGRIT L-30D | 15 g (Solids) (15.4% w/w based on antigen loaded beads; 70% w/w based on total polymer & Plasticizer solids) | 51.3 |
| TEC (Triethyl Citrate) | 3.3 g Solids) (3.3% w/w based on antigen loaded beads; 15% w/w based on total polymer & Plasticizer solids) | 3.3 |
| DBS (Dibutyl sebacate) | 3.3 g (Solids) (3.3% w/w based on antigen loaded beads; 15 w/w based on total polymer & plasticizer solids) | 3.3 |
| Talc | 1.1 g (5% w/w based on total polymer & plasticizer solids) | 1.1 |
| Water | N/A | 51.3* |

Enteric coating increased weight of microspheres to a final weight of about 123.1 g.
Total enteric-coating solids = 21.3% w/w based on dried antigen loaded beads.
*Water was added to make the final suspension about 20% w/v.

TABLE 4

ENTERIC-PROTECTED FILM POLYMER FORMULATION FOR 100 G OF 25–30 MESH-SIZE ANTIGEN-COATED VACCINE BEADS

| COMPONENTS | GRAMS | WT. IN DISPERSION |
|---|---|---|
| EUDAGRIT L-30D | 14 g (Solids) (14.0% w/w based on antigen loaded beads; 70% based on total polymer & Plasticizer solids) | 46.7 |
| TEC (Triethyl Citrate) | 3.0 g (Solids) (3.0% w/w based on antigen loaded beads; 15% w/w based on total polymer & Plasticizer solids) | 3.0 |
| DBS (Dibutyl sebacate) | 3.0 g (Solids) (3.3% w/w based on antigen loaded beads; 15 w/w based on total polymer & plasticizer solids) | 3.0 |

TABLE 4-continued

ENTERIC-PROTECTED FILM POLYMER FORMULATION FOR 100 G OF 25–30 MESH-SIZE ANTIGEN-COATED VACCINE BEADS

| COMPONENTS | GRAMS | WT. IN DISPERSION |
|---|---|---|
| Talc | 1.0 g (5% w/w based on total polymer & plasticizer solids) | 1.0 |
| Water | N/A | 46.7* |

Enteric coating increased weight of microspheres to a final weight of about 121 g.
Total enteric-coating solids = 21% w/w based on dried antigen loaded beads.

TABLE 5

ENTERIC-PROTECTED FILM POLYMER FORMULATION FOR 100 G OF 20–25 MESH-SIZE ANTIGEN-COATED VACCINE BEADS

| COMPONENTS | GRAMS | WT. IN DISPERSION |
|---|---|---|
| EUDAGRIT L-30D | 11.9 g (Solids) (11.9% w/w based on antigen loaded beads; 70% based on total polymer & Plasticizer solids) | 39.7 |
| TEC (Triethyl Citrate) | 2.55 g (Solids) (3.0% w/w based on antigen loaded beads; 15% w/w based on total polymer & Plasticizer solids) | 2.55 |
| DBS (Dibutyl sebacate) | 2.55 g (Solids) (3.3% w/w based on antigen loaded beads; 15 w/w based on total polymer & plasticizer solids) | 2.55 |
| Talc | .85 g (5% w/w based on total polymer & plasticizer solids) | 0.85 |
| Water | N/A | 39.7* |

Enteric coating increased weight of microspheres to a final weight of about 117.9 g.
Total enteric-coating solids = 17.9% w/w based on dried antigen loaded beads.

TABLE 6

ENTERIC-PROTECTED FILM POLYMER FORMULATION FOR 100 G OF 14–18 MESH-SIZE ANTIGEN-COATED VACCINE BEADS

| COMPONENTS | GRAMS | WT. IN DISPERSION |
|---|---|---|
| EUDAGRIT L-30D | 7.7 g (Solids) (7.7% w/w based on antigen loaded beads; 70% w/w based | 25.7 |

TABLE 6-continued

ENTERIC-PROTECTED FILM POLYMER FORMULATION FOR
100 G OF 14–18 MESH-SIZE ANTIGEN-COATED VACCINE BEADS

| COMPONENTS | GRAMS | WT. IN DISPERSION |
|---|---|---|
| | on total polymer & Plasticizer solids) | |
| TEC (Triethyl Citrate) | 1.65 g (Solids) (1.65% w/w based on antigen loaded beads; 15% w/w based on total polymer & Plasticizer solids) | 1.65 |
| DBS (Dibutyl sebacate) | 1.65 g (Solids) (1.65% w/w based on antigen loaded beads; 15 w/w based on total polymer & plasticizer solids) | 1.65 |
| Talc | .55 g (5% w/w based on total polymer & plasticizer solids) | 0.55 |
| Water | N/A | 25.7* |

Enteric coating increased weight of microspheres to a final weight of about 111.6 g.
Total enteric-coating solids = 11.6% w/w based on dried antigen loaded beads.

Table 7 lists typical parameters that were used to coat the microspheres using the Labline/PRL spray coater.

TABLE 7

TYPICAL PROCESS CONDITIONS FOR
ANTIGEN OR ENTERIC-FILM COATING

| Parameter | Amount or Setting |
|---|---|
| Bed load | 100 grams |
| Wurster Insert | bottom spray |
| Pump | peristaltic |
| Column | 7" Wurster |
| Nozzle Size | 0.8 mm |
| Inlet Temperature | 40 or 65° C. |
| Atomization Air | 15–18 psi |
| Fluidization air blower | 40–50% of capacity |
| Flow Rate | 2.3–6.5 ml/min intermittently* |
| Spray Time | 0.5–1.5 hour |
| Dry Time | about 15 minutes |
| Coating Level | very |

*Peristaltic pump was manually turned on or off as necessary to control clumping of beads during the coating process.

Vaccines also have been made which included adjuvants, such as immunostimulants. Immunostimulants were added to prime the immune system of the fish to enhance the immune response that occurs as a result of administering the vaccine of the present invention. β-glucans, which function well as adjuvants, are commercially available in molecular weights of from about 150,000 to about 700,000. It currently is believed that all such β-glucans are useful for forming vaccines according to the present invention. Thus, the method for forming ECAMs as described above can be modified to include a β-glucan adjuvant. One embodiment of a method for producing ECAMs utilizing β-glucans involved spray coating the sugar beads with p57⁻ cells, a thin coat of AQUACOAT brand coating agent, over which about 140 mg of β-glucan per 100 grams of beads was applied. The beads were then spray-coated with the EUDRAGIT L-30D enteric coating.

One embodiment of a β-glucan-containing vaccine is summarized below in Tables 8 and 9. The data provided in Table 8 represents the materials used in an AQUACOAT layer, and Table 9 provides the materials used to form the enteric-coating layer. The process for coating the beads first involved coating microspheres with vaccine, sodium starch glycolate, and gelatin to produce 160 grams of vaccine-loaded beads. A layer of an AQUACOAT composition was then applied over the first microsphere-coating layer. A layer of a β-glucan having a molecular weight of about 415,000 was then applied over the AQUACOAT layer. A solution of the β-glucan (10 mg/ml) was sprayed on the microspheres until 224 mg of the β-glucan was applied to the beads. Finally, the microspheres were coated with the enteric-coating composition as summarized in Table 9.

TABLE 8

AQUACOAT COMPOSITION FOR COATING MICROSPHERES

| COMPONENTS | GRAMS | WT. IN DISPERSION |
|---|---|---|
| AQUACOAT ® | 1.6 g (Solids) (1.0% w/w based on antigen loaded beads; 70% based on total polymer & Plasticizer solids) | 5.33 |
| TEC (Triethyl Citrate) | 0.24 g (Solids) (.15% w/w based on antigen loaded beads; 11.5% w/w based on total polymer & Plasticizer solids) | 0.24 |
| DBS (Dibutyl sebacate) | 0.24 g (Solids) (.15% w/w based on antigen loaded beads; 15 w/w based on total polymer & plasticizer solids) | 0.24 |

TABLE 9

ENTERIC COATING FOR BEADS FIRST
COATED WITH AQUACOAT

| COMPONENTS | GRAMS | WT. IN DISPERSION |
|---|---|---|
| EUDAGRIT L-30D | 24.6 g (Solids) (24.6% w/w based on antigen loaded beads; 70% w/w based on total polymer & Plasticizer solids) | 82.1 |
| TEC (Triethyl Citrate) | 5.3 g (Solids) (5.3% w/w based on antigen loaded | 5.3 |

TABLE 9-continued

ENTERIC COATING FOR BEADS FIRST COATED WITH AQUACOAT

| COMPONENTS | GRAMS | WT. IN DISPERSION |
|---|---|---|
| | beads; 15% w/w based on total polymer & Plasticizer solids) | |
| DBS (Dibutyl sebacate) | 5.3 g (Solids) (5.3% w/w based on antigen loaded beads; 15 w/w based on total polymer & plasticizer solids) | 5.3 |
| Talc | 1.75 g (5% w/w based on total polymer & plasticizer solids) | 1.75 |
| Water | |

Fish were considered to be infected with *Renibacterium salmoninarum* if the detected level of antigen was at least 3 ng/ml or greater.

The data obtained from these ELISA evaluations was statistically analyzed to determine if there were any significant differences between controls and fish treated with vaccines according to the present invention. These results are presented below in Tables 10 and 11. There appeared to be considerable variance between p57 levels in the challenged fish; therefore, all data was log transformed. The results shown below indicate that there was no statistically important difference between control studies and vaccinated fish prior to about 90 days. However, at ninety days the mean p57 levels (ng/ml) for the vaccinated fish was about 20 ng/ml, whereas the control had mean protein levels of about 351 ng/ml. At 150 days the statistical analysis clearly demonstrates that the fish treated orally with p57⁻ cells had a significant decrease in the levels of p57, thereby demonstrating the efficacy of vaccines produced according to the present invention.

Table 11 shows the results of serum antibody titers, expressed in activity/µl, throughout the testing period. These results demonstrate that the serum activity levels for p57⁻ orally treated fish were much lower than for control fish, or for fish treated by other methods. Specifically, p57⁻ orally treated fish had an activity of about 126 units/µl, whereas the mean value for the control fish was about 2060 units/µl.

described by Arkoosh and Kaattari (1990) *Quantitation of Fish Antibody to a Specific Antigen by an Enzyme Linked Immunosorbent Assay (ELISA), Techniques in Fish Immunology*, pp. 15–24, which is incorporated herein by reference. Each antiserum was titrated on an ELISA plate that was obtained from Costar E.I.A./R.I.A., Certified Surface Chemistry of Cambridge, Mass. Formalin-fixed *Renibacterium salmoninarum* was used as a coating agent at a concentration of approximately 150 µg/ml. Each plate contained a titration of an anti*Renibacterium salmoninarum* hyperimmune-serum.

Generally, the detection of serum antibodies is considered a measure of immunity. However, the results of the serum antibody titers seem to indicate that serum antibodies are not necessarily an indication of immunity in the vaccinated fish. Fish receiving oral vaccines survived *Renibacterium salmoninarum* challenge, but typically had lower serum antibody levels than fish receiving an IP injection. Fish receiving IP injections did exhibit an increased mean-time-to death. All treatment groups, other than the ECAM-delivered p57⁻ whole cells and the orally administered, non-pH protected p57⁻ whole cells, had significantly higher occurrences of p57 in the kidneys of fish challenged with *Renibacterium salmoninarum*.

Without limiting the present invention to one theory of

TABLE 10

Values expressed are the means of p57 detected (ng/ml) for each particular treatment at each sampling date. Standard errors are in parentheses. Asterisk denotes significant difference from control p < 0.01, ** = p < 0.03 versus control.

| Treatment | number of fish | Mean pre-challenge | mean 50 days post challenge | mean 90 days post challenge | mean 150 days post challenge |
|---|---|---|---|---|---|
| [a]Control | 15/sample day | <3 ng/ml[#] | 2.4 (.34) | 351 (352) | 2070 (1600) |
| [b]Oral p57– | 15/sample day | <3 ng/ml | 1.2 (.2) | 20 (18) | 1.9 (.419)* |
| [c]NPP p57– | 15/sample day | <3 ng/ml | 1.9 (.51) | 21 (17) | 2.9 (.59)** |
| [d]Oral p57+ | 15/sample day | <3 ng/ml | 1.3 (.3) | 8701 (8600) | 8403 (5603) |
| [e]ip p57– | 15/sample day | <3 ng/ml | 2.14 (.94) | 12900 (6400) | 220 (173) |

[a] = control non-antigen coated beads.
[b] = ECAM delivered p57– whole cells.
[c] = Non-pH protected p57– whole cells.
[d] = p57+ whole cells.
[e] = intraperitoneal injected p57– whole cells.
[#] = below detection limit of assay.

TABLE 11

Values expressed are the means of serum antibody units of activity/µl serum detected for each particular treatment at each sampling date. Standard errors are in parentheses.

| Treatment | number of fish | Mean pre-challenge | mean 50 days post challenge | mean 90 days post challenge | mean 150 days post challenge |
|---|---|---|---|---|---|
| [a]Control | 15/sample day | -ND-[#] | -ND- | 2060 (226) | 2060 (2276) |
| [b]Oral p57– | 15/sample day | -ND- | -ND- | -ND- | 126 (436) |
| [c]NPP p57– | 15/sample day | -ND- | -ND- | 938 (2241) | 1827 (3146) |
| [d]Oral p57+ | 10/sample day | -ND- | -ND- | 500 (1881) | 3423 (5852) |
| [e]ip p57– | 15/sample day | 5800 (1500) | 42400 (52030) | 82000 (210000) | 14776 (22065) |

[a] = control non-antigen coated beads.
[b] = ECAM delivered p57– whole cells.
[c] = Non-pH protected p57– whole cells.
[d] = p57+ whole cells.
[e] = intraperitoneal injected p57– whole cells.
[#] = below detection limit of assay.

J. Determination of Antibody Activity

Antibody activity titers were ascertained by the use of an enzyme-linked immunosorbent assay (ELISA) as previously operation, it appears that the best vaccination results are obtained by inducing mucosal immunity. As a result, serum antibody levels are of less importance than mucosal antibody levels. Alternatively, it may be that the protective response in the fish is not mediated by antibodies.

The present invention has been described with reference to several preferred embodiments. Other embodiments of the invention will be apparent to those skilled in the art from a consideration of this specification or practice of the invention disclosed herein. It is intended that the specification and examples contained herein be considered as exemplary only, with the true scope and spirit of the invention being indicated by the following claims.

We claim:

1. A vaccine for treating fish susceptible to infection by *Renibacterium salmoninarum* comprising killed *Renibacterium salmoninarum* microorganisms lacking substantially all intact cell-surface-associated protein p57.

2. The vaccine according to claim 1 and further including a material selected from the group consisting of adjuvants, plasticizers, pharmaceutical excipients, antigens other than cells lacking substantially all intact cell-surface-associated protein p57, diluents, carriers, binders, lubricants, glidants and aesthetic compounds, and combinations thereof.

3. The vaccine according to claim 1 wherein the *Renibacterium salmoninarum* microorganism is *Renibacterium salmoninarum* ATCC strain 33209.

4. The vaccine according to claim 1 comprising an enteric coating.

5. The vaccine according to claim 4 wherein the enteric coating is impervious to dissolution in a stomach of the fish.

6. The vaccine according to claim 4 wherein the enteric coating is selected from the group consisting of polymeric enteric coating materials that dissolve in a liquid having a pH of about 5 or greater.

7. The vaccine according to claim 4 wherein the enteric-coating material is a polymeric enteric coating material that dissolves in a liquid having a pH of about 5 or greater, and less than about 8.

8. The vaccine of claim 1, wherein the vaccine is prepared by heating the *Renibacterium salmoninarum* microorganism at a sufficient temperature for a sufficient period of time to provide a killed microorganism that substantially lacks intact cell-surface associated protein p57.

9. The vaccine of claim 8, wherein the microorganism is heated at a temperature of 37°–55° C. for a sufficient period of time to kill the microorganism and substantially remove intact cell surface associated protein p57.

10. The vaccine of claim 9, wherein the microorganism is encapsulated by an enteric coating that dissolves to release the killed microorganism in a pH greater than 5.

11. The vaccine of claim 9, wherein the microorganism is encapsulated by an enteric coating that dissolves to release the killed microorganism in a pH of 5–8.

12. An oral vaccine for treating fish susceptible to infections by *Renibacterium salmoninarum* comprising:

killed *Renibacterium salmoninarum* microorganisms lacking substantially all intact cell-surface-associated protein p57; and an enteric coating that protects the *Renibacterium salmoninarum* microorganisms from degradation in a stomach of the fish.

13. The vaccine according to claim 12 wherein the microorganism is *Renibacterium salmoninarum* ATCC strain 33209.

14. An oral vaccine for treating fish susceptible to infection by *Renibacterium salmoninarum*, comprising:

microspheres having a mesh size of from about 10 to about 60 mesh;

a first microsphere coating layer comprising killed *Renibacterium salmoninarum* microorganisms lacking substantially intact cell-surface-associated protein p57; and at least a second microsphere coating layer comprising an enteric coating layer that is impervious to dissolution in a stomach of the fish.

15. The vaccine according to claim 14 and further including a material selected from the group consisting of adjuvants, plasticizers, pharmaceutical excipients, antigens other than cells lacking intact cell-surface-associated protein p57, diluents, carriers, binders, lubricants, glidants, and aesthetic compounds, and combinations thereof.

16. The vaccine according to claim 15 wherein the adjuvant is a disintegrant or a super disintegrant.

17. The vaccine according to claim 15 wherein the pharmaceutical excipient is a β-glucan.

18. The vaccine according to claim 15 wherein the enteric-coating layer comprises a polymeric organic material that dissolves in a liquid having a pH of about 5 or greater.

19. The vaccine according to claim 18 wherein the enteric-coating layer comprises poly(methylacrylic acid-ethyl acrylate).

20. The vaccine according to claim 15 wherein the enteric coating layer comprises from about 2 weight percent to about 50 weight percent poly(methylacrylic acid-ethyl acrylate), less than about 10 weight percent dibutyl sebacate, less than about 10 weight percent triethyl citrate, and talc.

21. An oral vaccine for treating fish susceptible to infection by *Renibacterium salmoninarum*, comprising:

microspheres having a mesh size of from about 25 mesh to about 30 mesh;

a coating layer comprising killed *Renibacterium salmoninarum* microorganisms lacking substantially all intact cell-surface-associated protein p57;

an enteric-coating layer comprising a polymeric organic material that is impervious to dissolution in a stomach of the fish; and a material selected from the group consisting of adjuvants, plasticizers, pharmaceutical excipients, antigens other than cells lacking substantially all intact cell-surface-associated protein p57, diluents, carriers, binder, lubricants, glidants, aesthetic compounds, and combinations thereof.

22. A vaccine for treating fish susceptible to infection by *Renibacterium salmoninarum*, comprising *Renibacterium salmoninarum* heated to a temperature of about 37° C. for about 48 hours.

* * * * *

UNITED STATES PATENT AND TRADEMARK OFFICE
CERTIFICATE OF CORRECTION

PATENT NO. : 5,871,751

DATED : Feb. 16, 1999

INVENTOR(S) : Christensen et al.

It is certified that error appears in the above-indentified patent and that said Letters Patent is hereby corrected as shown below:

Column 7, line 17, replace "Protein P57" with --Protein p57--;
Column 12, line 28, please format and center "EXAMPLE 4" as in "EXAMPLE 1."

<u>In the Claims</u>:

Claim 14, Column 22, line 11, insert after "stantially" --all--;
Claim 21, Column 22, line 53, replace "binder" with --binders--.

Signed and Sealed this

Twentieth Day of March, 2001

Attest:

NICHOLAS P. GODICI

Attesting Officer       Acting Director of the United States Patent and Trademark Office